United States Patent [19]

Ranalletta et al.

[11] Patent Number: 5,025,957
[45] Date of Patent: Jun. 25, 1991

[54] LIQUID DISPENSER NOZZLE ASSEMBLY

[75] Inventors: Joseph V. Ranalletta, Guntersville; Fred E. Williams, Jr., Arab; Rowland W. Kanner, Guntersville, all of Ala.

[73] Assignees: Ryder International Corp., Arab, Ala.; pK Scientific Inc., Frederick, Md.

[21] Appl. No.: 406,053

[22] Filed: Sep. 11, 1989

Related U.S. Application Data

[63] Continuation-in-part of Ser. No. 255,365, Oct. 7, 1988, abandoned.

[51] Int. Cl.⁵ .......................... B67D 5/58; B67D 37/00
[52] U.S. Cl. .................................. 222/189; 222/213; 222/494
[58] Field of Search ................. 604/294–298; 222/189, 209, 213, 215, 490–492, 494, 420, 421

[56] References Cited

U.S. PATENT DOCUMENTS

| | | | |
|---|---|---|---|
| 4,002,168 | 1/1977 | Petterson | 222/421 |
| 4,061,254 | 12/1977 | Nilson | 222/494 |
| 4,186,882 | 2/1980 | Szczepanski | 239/327 |
| 4,420,101 | 12/1983 | O'Neill | 222/494 |
| 4,474,314 | 10/1984 | Roggenburg, Jr. | 222/494 |
| 4,478,356 | 10/1984 | Roggenburg, Jr. | 222/494 |
| 4,533,068 | 8/1985 | Meirhoefer | 222/189 |
| 4,739,906 | 4/1988 | Loturco | 222/494 |
| 4,917,271 | 4/1990 | Kanner et al. | 222/189 |
| 4,930,667 | 6/1990 | Holzner, Sr. | 222/189 |

Primary Examiner—Robert P. Olszewski
Assistant Examiner—Steve Reiss
Attorney, Agent, or Firm—R. A. Giangiorgi

[57] ABSTRACT

A liquid dispensing nozzle assembly is provided for mounting on a liquid container and dispenser having a flexible wall and liquid storage cavity for manually squeezed dispensing of a liquid from the cavity through the nozzle assembly. The nozzle assembly maintains the liquid, such as contact lens saline solution, in sterile condition during storage and repeated dispensing of the liquid from the container cavity. The nozzle assembly includes a liquid conduit for communication from the container cavity to a liquid discharge port from the nozzle assembly to enable dispensing of the liquid displaced by manually squeezing the flexible wall of the container. The nozzle assembly also includes an air aspiration conduit separate from the liquid conduit for aspirating air into the container cavity to replace the dispensed liquid. The nozzle assembly includes a partitioned diaphragm including separate portions respectively included in the liquid conduit and the air aspiration conduit. The air conduit portion of the diaphragm can include a filter which is hydrophobic and air permeable but impermeable to bacteria to prevent entrainment of bacteria with the aspirating flow of air into the liquid storage cavity of the container.

45 Claims, 6 Drawing Sheets

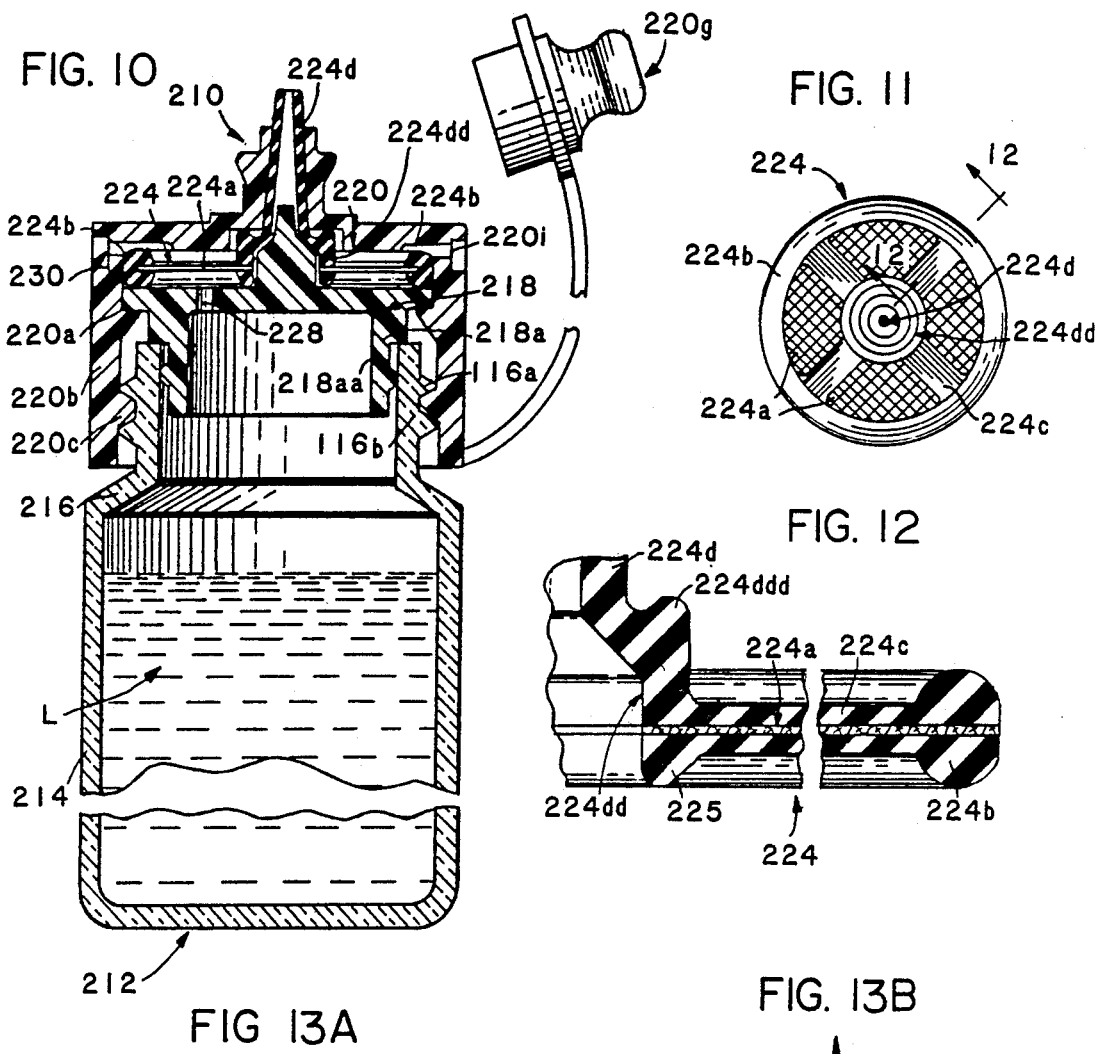
FIG. 10
FIG. 11
FIG. 12
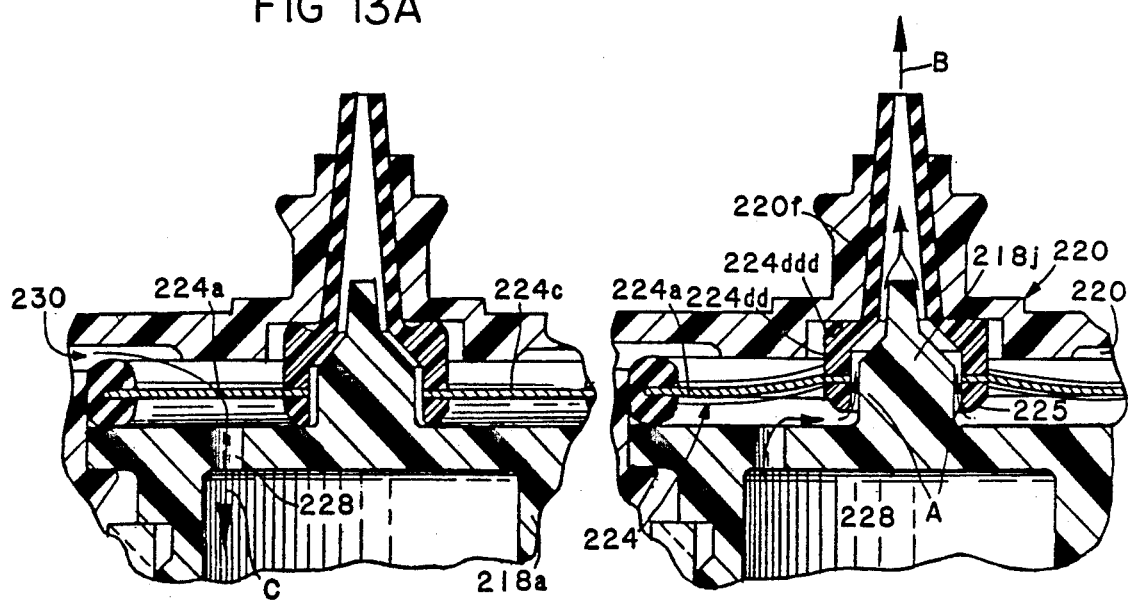
FIG. 13A
FIG. 13B

LIQUID DISPENSER NOZZLE ASSEMBLY

CROSS-REFERENCE TO RELATED APPLICATION

This application is a continuation-in-part of application Ser. No. 255,365 filed Oct. 7, 1988, now abandoned.

BACKGROUND OF THE INVENTION

The present invention relates to liquid storage containers for manually dispensing liquids such as cleaning solutions for contact lenses, and more particularly relates to dispensing nozzles on containers for liquid which must be stored in sterile condition.

Liquids, for example, solutions for cleaning and conditioning contact lenses, have typically been stored in manually squeezable bottles from which the user can repeatedly dispense the stored liquid. These liquids must be uncontaminated by microorganisms such as bacteria. Accordingly, expensive bacteriacidal agents have sometimes been included in liquid formulation, as for example, in saline formulations for cleaning contact lenses. Furthermore, the squeezable dispensing bottles have sometimes been provided with nozzles including filter membranes which are permeable to the dispensed liquid as well as being permeable to the air which must be aspirated through the nozzle to replace the dispensed liquid. These filter membranes are also impermeable to bacteria in order to prevent the aspirated air from carrying bacteria into contact with the stored solution, so that the solution is maintained in sterile condition for repeated dispensing. However, filter membrane materials which are sufficiently hydrophilic to permit permeation of the saline solutions often permit retention of the saline on the filter so that the retained solution increases the resistance of the filter to passage of the aspirating air. The partially obstructed flow of aspirating air not only retards the expansion of the squeezed bottle wall, but also impedes a subsequent squeezing of the bottle when a demand for large quantities of the solution must be dispensed.

In accordance with this invention, a nozzle assembly provides accelerated air aspiration of the squeezed liquid dispensing bottle for improved convenience to the user, particularly in repeated dispensing of the solutions for contact lenses.

SUMMARY OF THE INVENTION

According to the subject invention, a liquid dispensing nozzle assembly is provided for mounting on a liquid container and dispenser having a flexible wall and liquid storage cavity for manually squeezed dispensing of liquid from the cavity through the nozzle assembly. The nozzle assembly maintains the liquid, such as contact lens saline solution, in sterile condition during storage and repeated dispensing of the liquid from the container cavity The nozzle assembly includes a liquid conduit for communication from the container cavity to a liquid discharge port from the nozzle assembly to enable dispensing of the liquid displaced by manually squeezing the flexible wall of the container. The nozzle assembly also includes an air aspiration conduit separate from the liquid conduit for aspirating air into the container cavity to replace the dispensed liquid. The nozzle assembly includes a partitioned diaphragm including separate portions respectively included in the liquid conduit and the air aspiration conduit.

In preferred embodiment, the nozzle assembly includes an integrally molded, elastomeric diaphragm which includes a deflectable valve element within the liquid conduit. The valve element normally closes a one-way valve to prevent leakage of the liquid from the container cavity. The valve element deflects with liquid pressure on the diaphragm to open the valve so that liquid flows through the valve and is discharged from the liquid conduit. The diaphragm includes a tubular nozzle which provides the liquid discharge orifice for the liquid dispensed from the conduit The preferred nozzle assembly embodiment also include an integral diaphragm filter portion which is hydrophobic in order to prevent permeation of the filter portion by the stored liquid, which further facilitates the aspirating air flow through the filter and the air conduit Both the diaphragm and the filter member are clamped between an adapter member and an overlying housing member provided in the nozzle assembly which are secured at the neck opening of the container. The filter portion is air permeable but impermeable to bacteria to prevent entrainment of bacteria with the aspirating flow of air into the liquid storage cavity of the container.

BRIEF DESCRIPTION OF THE DRAWINGS

The features of the present invention which are believed to be novel are set forth with particularity in the appended claims. The organization and manner of operation of the invention, together with further objects and advantages thereof, may best be understood by reference to the following description taken in connection with the accompanying drawings in which like reference numerals identify like elements, and in which:

FIG. 10 is a vertical sectional view of a third embodiment of the liquid nozzle assembly of the invention, mounted on a liquid storage and dispensing container;

FIG. 11 is a top plan view of an integral combination diaphragm and air aspiration filter shown in FIG. 10;

FIG. 12 is an enlarged fragmentary sectional view of a section of the diaphragm as indicated in the line 12—12 in FIG. 11;

FIG. 13A is an enlarged, fragmentary sectional view of the nozzle assembly shown in FIG. 10 and illustrating the flow path for air aspiration through the nozzle assembly; and FIG. 13B is an enlarged, fragmentary sectional view similar to FIG. 13A, which illustrates the liquid flow path through the nozzle assembly.

DETAILED DESCRIPTION OF THE ILLUSTRATED EMBODIMENT

Figure 1:
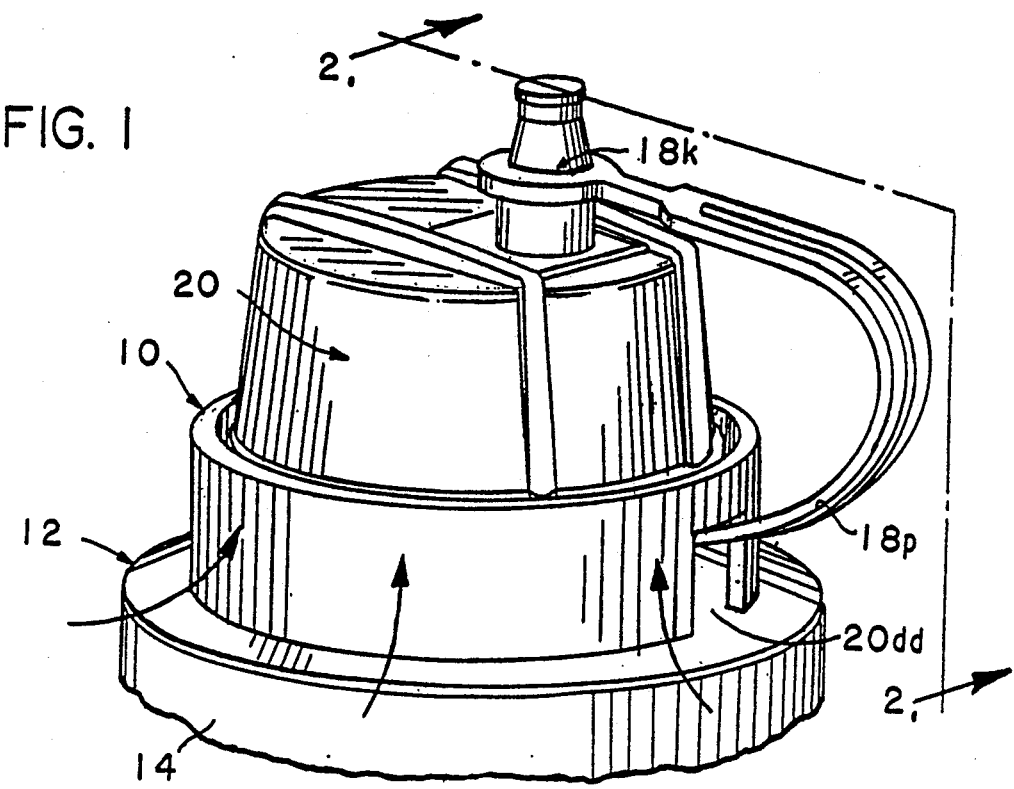
FIG. 1 is a perspective view of an embodiment of the liquid nozzle assembly of the invention mounted on a liquid storage and dispensing container.
Figure 2:
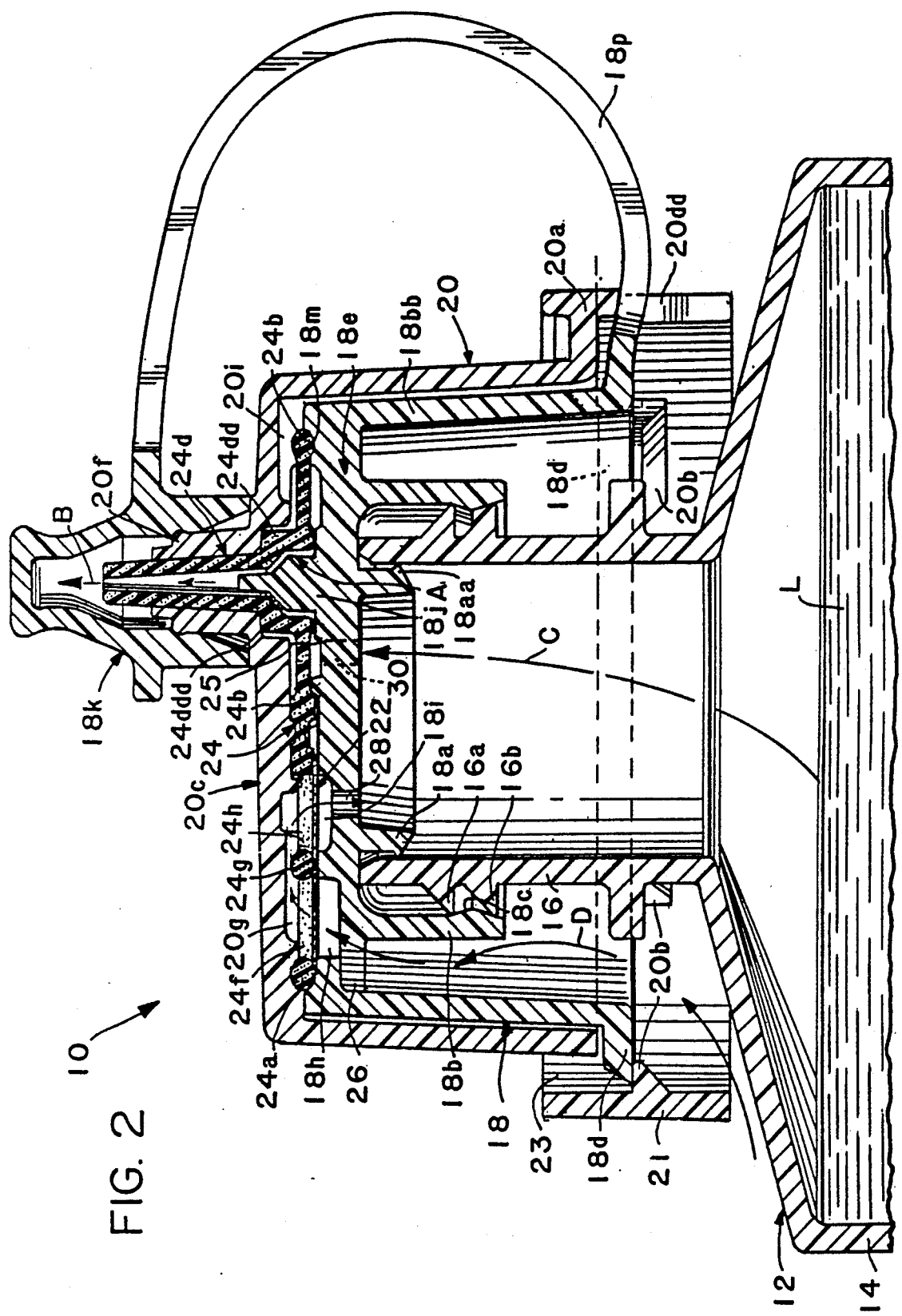
FIG. 2 is a sectional view taken along each of the lines indicated at 2—2 in FIGS. 1, 4, and 6.

Referring to FIGS. 1 and 2, an embodiment of the nozzle assembly in accordance with the invention and designated generally by reference character 10 is shown mounted on a molded plastic bottle or liquid container 12 having a flexible or squeezable wall 14 and containing liquid such as saline solution. As shown in FIG. 2, the container 12 opens at the top from a neck portion 16. A generally cylindrical adapter 18 surrounds the neck portion 16. The adapter 18 includes an annular, internal flange 18a which projects downwardly into the opening at the top of the neck 16 and terminates in a radially flared annular projection 18aa which securely engages, and preferably forms a seal with, the interior surface of the neck. The adapter 18 has a medial cylindrical skirt 18b which has an inwardly extending, annular lug 18c which is forced between a pair of adjacent, radially outwardly extending annular flanges 16a, 16b which enable an interference fit with the lug 18c therebetween to securely mount the adapter 18 on the bottleneck 16 in a sealed condition.

Figure 4:
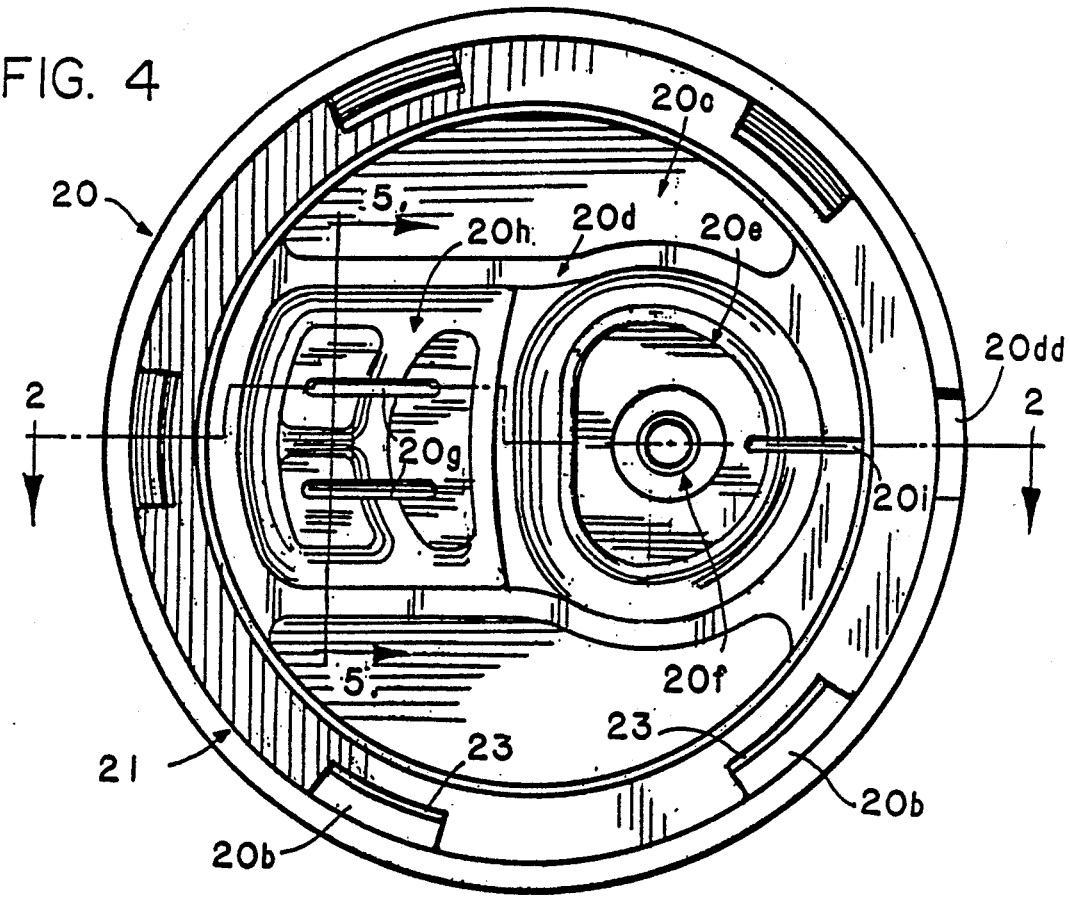
FIG. 4 is a bottom plan view of a nozzle housing of the assembly as indicated by the line 4—4 in FIG. 3.
Figure 3:
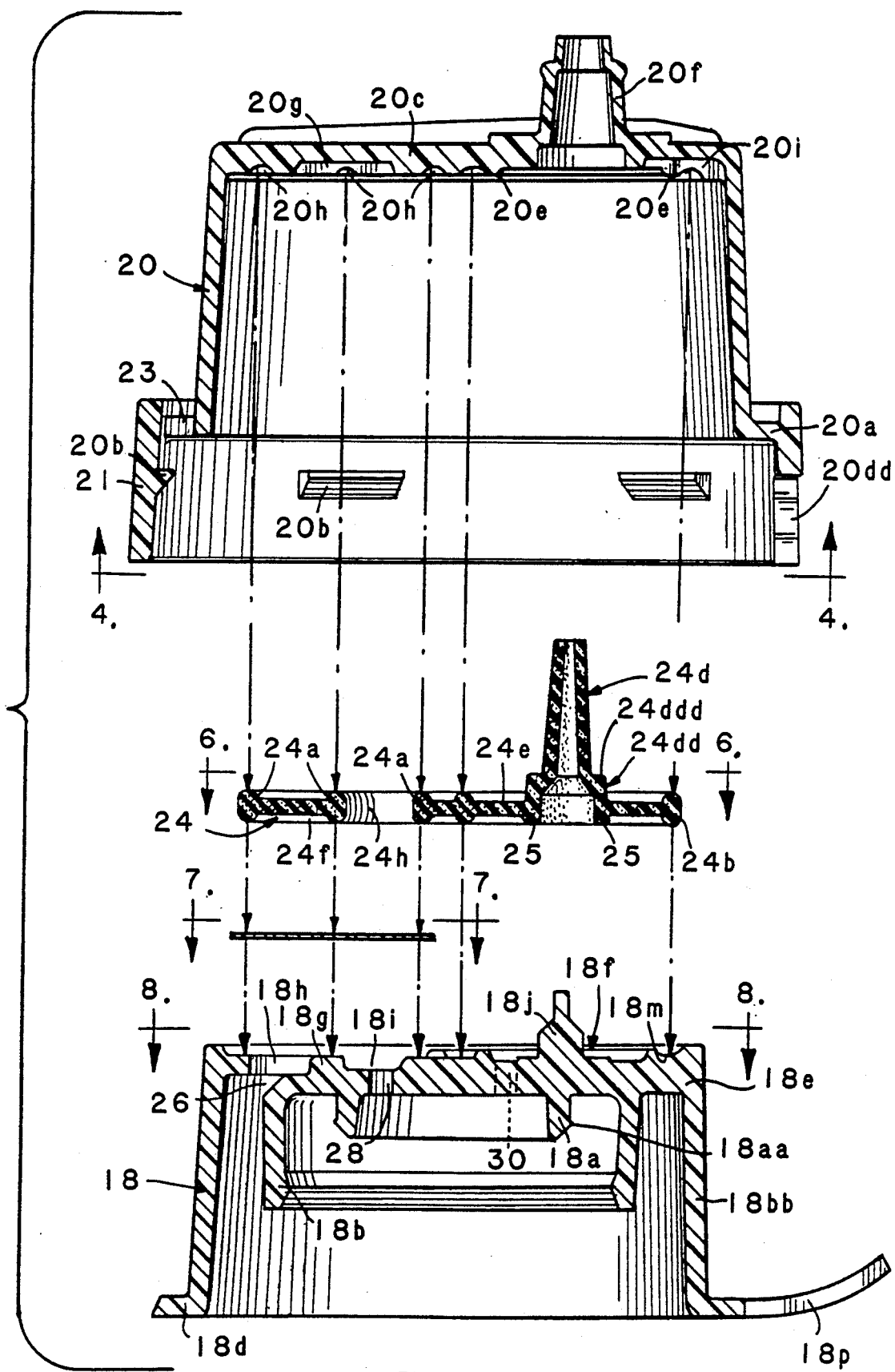
FIG. 3 is an exploded, sectional view of the nozzle assembly in FIGS. 1 and 2.

A radially outwardly extending annular flange 18d forms a shoulder at the bottom of a radially outermost skirt 18bb and the shoulder flange 18d forms a base on which a generally cylindrical nozzle housing or cap 20 is seated. The flange 18d is snap-fit and clamped between an annular shoulder 20a of the nozzle housing 20 and an annular arrangement of six spaced arcuate cleat portions 20b projecting inwardly from a lowermost annular skirt portion 21 of the housing 20 as shown in FIGS. 2–4. Also as shown in FIGS. 2–4, the shoulder wall 20a is interrupted by an annular arrangement of six through-slots 23 which are respectively aligned with the six cleats 20b; slots 23 provide tooling access for molding the cleats.

Figure 6:
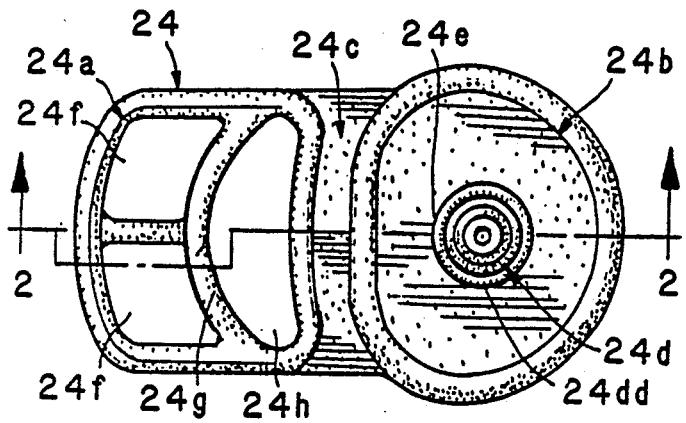
FIG. 6 is a top plan view of a diaphragm element as indicated by the line 6—6 in FIG. 3.
Figure 7:
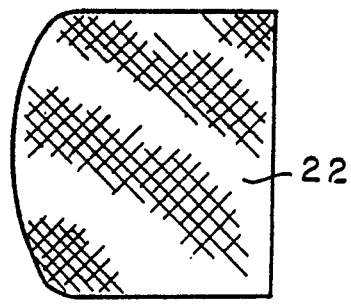
FIG. 7 is a top plan view of a filter element as indicated by the line 7—7 in FIG. 3.
Figure 8:
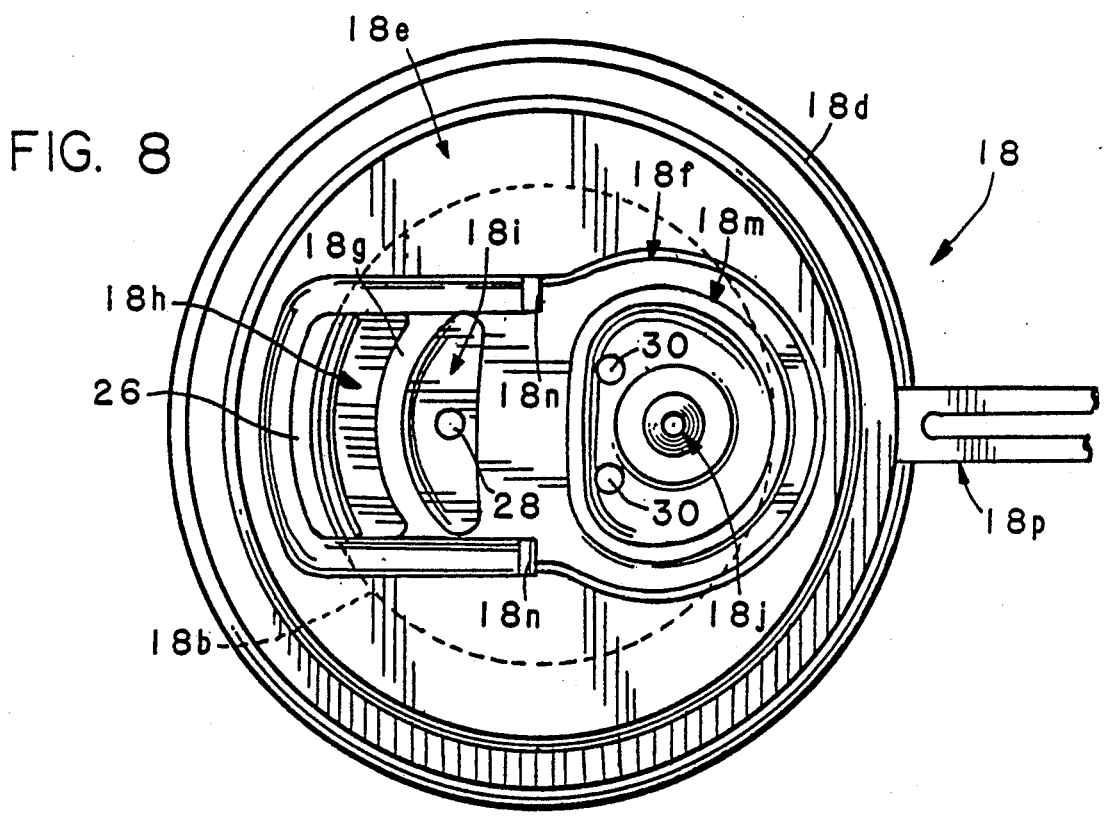
FIG. 8 is a top plan view of an adapter element as indicated by the line 8—8 in FIG. 3.

Referring to FIGS. 2, 3 and 8, the adapter 18a includes a circular upper wall designated generally by reference character 18e which is divided into separate portions providing for separate and distinct liquid dispensing conduit means and air aspiration conduit means. The upper wall 18e also forms a base which seats a hydrophobic filter member 22 and a complex, elastomeric diaphragm 24 integrally molded, for example from silicone rubber, as shown in FIGS. 2, 2A, 3 and 6. As best shown in FIGS. 3 and 8, the upper wall 18e of the adapter 18 has a recess 18f which peripherally conforms to and positions the diaphragm 24 as shown in FIG. 6. As indicated in FIG. 3 and shown in FIG. 2, the filter member 22 (FIG. 7) is seated and clamped within a left-handed portion of the recess 18f by a left-hand portion of the diaphragm 24 (i.e., left-hand as viewed in FIGS. 2, 6 and 8). As best shown in FIGS. 2 and 8, a medial arcuate bridging surface 18g within the recess 18f divides two deeper recesses 18h and 18i which are covered by the filter member 22; an arcuate slot 26 is formed through the wall 18e radially outside the medial skirt 18b, and extends into the recess 18h to form a portion of an intake conduit for air aspiration together with a bore 28 from the recess 18i through the wall 18e, as more fully described hereinafter.

Figures 2A, 9:
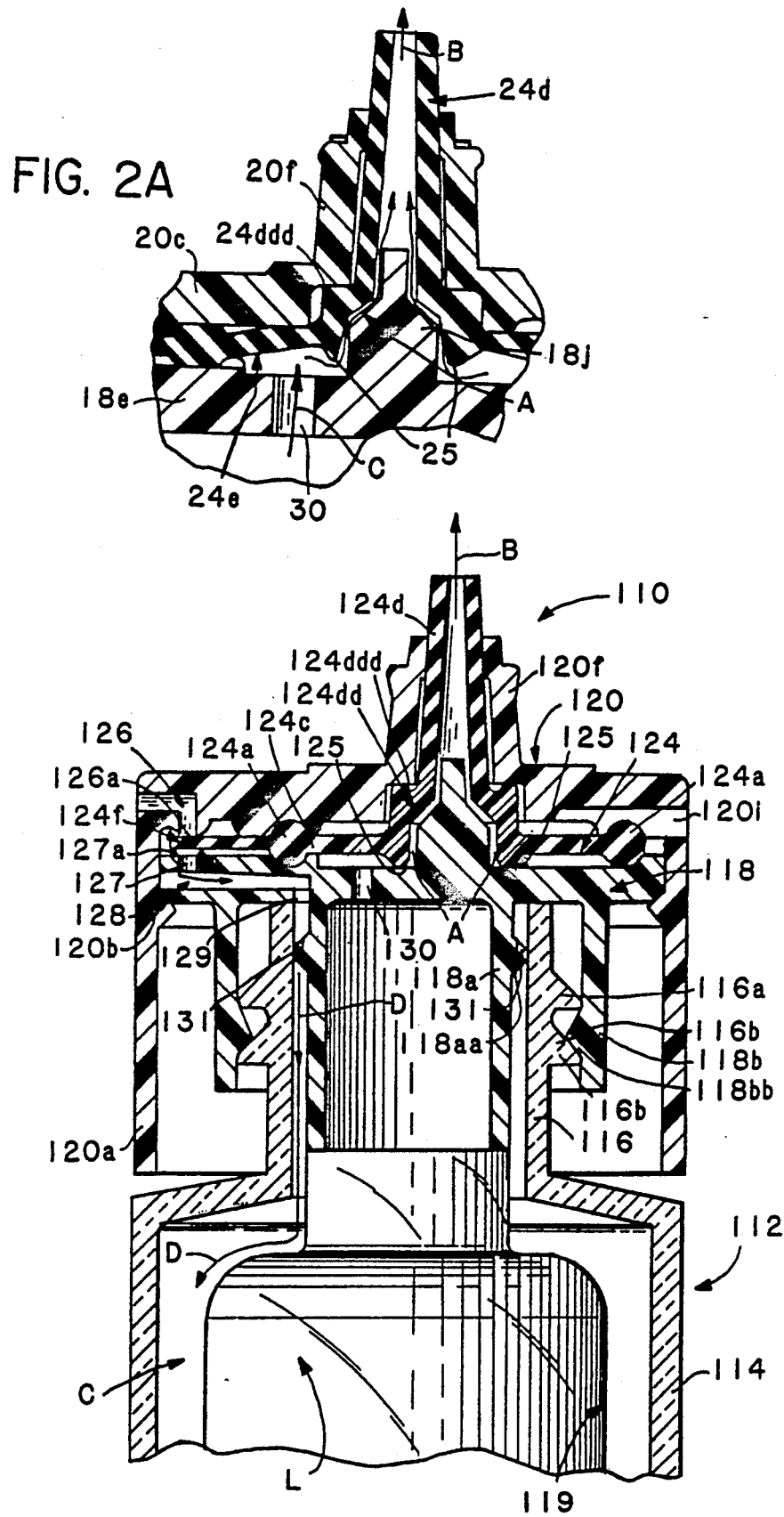
FIG. 2A is an enlarged fragmentary view taken from FIG. 2 and illustrating the deflection of a valve element to open a liquid dispensing conduit in the nozzle assembly.
FIG. 9 is a vertical sectional view of a second embodiment of the liquid nozzle assembly in accordance with the invention, mounted on a liquid storage and dispensing container.

Referring to FIG. 6, the illustrated embodiment of the diaphragm 24 includes two thickened, peripheral beads 24a and 24b which are separated by a small diaphragm web 24c. As shown in FIG. 2, the separate beads 24a and 24b are clamped within the recess 18f by an inner surface of the upper circular cap wall 20c. The cap wall 20c also has a molded embossment 20d shown in FIG. 4 which provides peripherally conformed surrounding engagement with the clamped diaphragm beads. A second, radially inner embossment 20e is configured to fit within and position the oval bead 24b. As shown in FIGS. 2 and 6, the diaphragm 24 further includes a frustoconical, tubular nozzle portion 24d which integrally extends upwardly from a larger elastomeric, tubular column or valve portion 24dd. The interior surface of the columnar valve base portion 24dd fits loosely around a nipple formation 18j projecting upwardly from the adapter wall 18e to provide a conical, annular clearance space A therebetween as shown in FIGS. 2 and 2A. The clearance space A leads to the central bore of the tubular portion 24d which provides at its upper end a discharge orifice for the liquid dispensing conduit as indicated by the arrow B and as more fully described hereinafter. The tubular nozzle 24d is supported by a surrounding annular boss 20f whose lower surface seals against the annular upper surface 24ddd of the tubular base 24dd as shown in FIG. 2 and 2A and more fully discussed hereinafter with the valve operation.

Referring again to FIG. 8, two bores 30 through the adapter wall 18e adjacent the nipple 18j provide passageways for liquid flow in the liquid dispensing conduit as indicated by the arrow C in FIG. 2 and leading to the clearance passageway A and then to the discharge indicated by B when a snap-fitting cover 18k is removed from the nozzle housing 20. The cover 18k has a cup-like configuration and is connected by an integrally molded connecting web or lanyard 18p which is flexible and joined to a portion of the annular adapter shoulder 18d and passes through a notch 20dd formed in the skirt 21 of the nozzle housing 20 as best shown in FIG. 1.

The tubular column or valve portion 24dd extends downwardly and terminates in a tapered sealing ring 25 which normally seals, under compression by the boss 20f, against the adapter wall 18e at its surface surrounding the nipple 18j to prevent leakage of the stored liquid (saline solution) even under hydrostatic pressure when the container is inverted in handling, and to prevent any backflow of non-sterile air or liquid from the clearance space A into the bottleneck 16. Backflow liquid is additionally prevented by the projection of the conically shaped nipple 18j into the tubular nozzle portion 24d in order to minimize the volume of liquid remaining in the tubular portion 24d when the dispensing flow has stopped. The small amount of remaining liquid in the tubular portion 24d, which can be exposed to contamination by air, will be flushed out before the next dispensing.

Referring to FIG. 2A, when the flexible wall 14 is squeezed to dispense the saline solution from the inverted container 12 and nozzle assembly 10, the liquid flows through both of the passageway bores 30 and exerts the necessary threshold hydraulic pressure against the diaphragm portion 24e which is resiliently deflected to further compress the tubular valve portion 24dd against the boss 20f; the additional compression of the valve portion 24dd thereby displaces and unseats sealing ring 25 from wall 18e to enable the liquid flow therebetween into the adjacent portion of the annular clearance space A (which is enlarged by the diaphragm deflection). The liquid flow through the clearance space A leads to discharge of the liquid through the tubular nozzle 24d as indicated by the arrow B. The sealing ring 25 perform as a one-way valve allowing only outflow of dispensed liquid when the flexible wall 14 is squeezed, so that once the additional compression of the valve portion 24dd is relaxed when the manual squeeze is released, the residual compression of the valve portion 24dd will cause the sealing ring 25 to reseat and firmly seal against the wall 18e to close the one-way valve and prevent any backflow of liquid or air, for example, should the dispenser become exposed to non-sterile fluid such as by dropping into contaminated liquid. The valve portion column 24dd thus acts as an integral and elastomeric biasing spring on the sealing ring 25.

The liquid flowing from the bores 30 is constrained to enter the conical clearance space A by the circumscribing seal provided by the clamped oval diaphragm bead 24b. The seal provided by the diaphragm bead 24b is positioned and reinforced by a seating groove 18m and the two slightly projecting shoulders 18n which are formed within the adapter recess 18f as shown in FIG. 2 and best shown in FIG. 8. The cap wall 20c has a narrow vent groove 20i shown in FIGS. 2 and 4 which is located on the dry or non-liquid side above the diaphragm 24 to enable air displacement with the deflection of the diaphragm.

Figure 5:
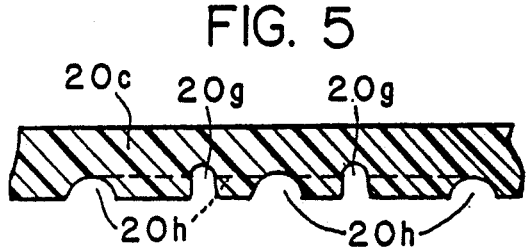
FIG. 5 is a fragmentary, sectional view taken along the line 5—5 in FIG. 4 and viewed in the indicated direction.

Referring to FIGS. 2 and 4, in order to aspirate air for reinflation of the squeezed flexible wall 14 and to replace the liquid dispensed, ambient air is drawn under or around the housing skirt 21 upwardly through the nozzle assembly and downwardly into the bottleneck 16. The detailed air flow path leads from the skirt 21 through the slot 26 and into the recess 8h as indicated by the series of upwardly pointing arrows D in FIG. 2; from the recess 18h, the air passes through the left portion of the hydrophobic and air permeable filter membrane 22 as viewed in FIG. 2. The upwardly flowing air from the filter membrane 22 then flows through the two side-by-side apertures 24f (both of which are shown in FIG. 6). From each of the apertures 24f the air passes into a respective one of parallel groove channels 20g which are molded into the lower surface of the housing wall 20c as best shown in FIGS. 4 and 5. The groove channels 20g direct the horizontal flow of air above a medial transverse bridge portion 24g of the diaphragm bead 24a. Bead 24a and bridge 24g fit into a complementary groove 20h in housing 20, shown in FIG. 4. The air from both groove channels 20g flows through the diaphragm aperture 24h and then flows downwardly through the filter membrane 22 again, whereupon the now twice-filtered air passes into the recess 18i and into the bore 28 leading to the bottleneck 16 for reinflation of the flexible wall 14.

The aspirating air is constrained to flow twice through the filter membrane 22, as indicated by the arrows in FIG. 2, by the clamped diaphragm bead 24a which circumscribes both the air aspiration slot 26 and the bore 28. The filter membrane 22 itself is hydrophobic to prevent passage of liquid (saline solution) from the bore 28 when the liquid is dispensed through the bores 30. The filter membrane is also impermeable to bacteria so that the aspirating air is filtered twice to prevent entrained bacteria from contaminating the stored saline solution. The saline solution is therefore maintained in sterile condition within the container 12 during repeated dispensing of the solution and air aspiration. Suitable air permeable hydrophobic filter material can be fabricated, for example, from supported acrylic copolymer treated with a siloxane composition such as the filter membrane material commercially available from Gelman Sciences in a particularly suitable composition designated Versapor-450 having a pore size of approximately 0.45 micron which is impenetrable to bacteria.

SECOND EMBODIMENT

Referring to FIG. 9, a second embodiment of the nozzle assembly in accordance with the invention and designated generally by reference character 110 is shown mounted on a molded plastic bottle or liquid container 112 having a flexible or squeezable wall 114. The container 112 opens at the top from the neck portion 116. A generally cylindrical adapter 118 of the nozzle assembly surrounds the neck portion 116. An adapter 118 has an annular internal flange 118a which projects downwardly into the opening of the neck 116 and has a radially flared annular projection 118aa which securely seals against the interior surface of the neck. In this embodiment, the sterile liquid L, such as saline solution, is contained within a flexible inner bag 119 whose mouth 119a is sealed to the adapter flange 118a so that the nozzle assembly 110 and bag 119 provide an integrally sealed container system with an elastomeric diaphragm 124 sealing out outside air and contamination from the interior of the bag 119 and a sterile liquid L. The elastomeric diaphragm 124 has a thickened, annular peripheral bead 124a which is clamped between an annular recess 118f in the upper surface of the adapter 118 and a similarly mating recess in the inner surface of the overlying housing or cap 120.

The cap 120 includes a downwardly extending, cylindrical skirt 120a which has an annular, inwardly projecting lug 120b wedged below the outer periphery of the adapter 118 which secures the clamping of the diaphragm. The adapter 118 has a radially outer cylindrical skirt 118b which also has a radially inwardly extending annular lug 118bb which is forced between a pair of adjacent annular coupling flanges 116a, 116b which enable an interference fit with lug 18bb therebetween to securely mount the adapter 118 and the nozzle assembly 110, generally on the bottle neck 16 in sealed position.

The diaphragm 124 integrally includes a tubular nozzle portion 124d which integrally extends upwardly from a larger elastomeric, tubular column or valve portion 124dd. The interior surface of the columnar valve portion 124dd fits loosely around a nipple formation 118j projecting upwardly from the adapter wall 118e to provide a conical, clearance space A therebetween. The clearance space A leads to the central bore of the tubular portion 124d which provides a liquid discharge orifice at it's upper end as indicated by arrow B. The tubular nozzle 124d is supported by an annular boss 120f whose lower surface seals against the annular upper surface 124ddd of the tubular valve portion 124dd. A snap-fitting cover (not shown) can be provided to removably fit over the tubular nozzle 124d and boss 120f, similar to the cap 18k provided in the first embodiment of the nozzle assembly.

The tubular column or valve portion 124dd extends downwardly and terminates in a tapered sealing ring 125 which normally seals, under compression by the boss 120f against the adapter wall 118e at its surface surrounding the nipple 118j to prevent leakage of the stored liquid even under hydrostatic pressure when the container 112 is inverted during handling, and to prevent any backflow of non-sterile air or liquid from the clearance space A into the bottle neck 116. Backflow of liquid is additionally prevented by the projection of the conically shaped nipple 118j into the tubular nozzle portion 124d in order to minimize the volume of liquid remaining in the tubular portion 124d when the dispensing flow is stopped. The small amount of remaining liquid in the tubular portion 124d, which can be exposed to contamination by air, will be flushed out before the next dispensing.

When the flexible container wall 114 is squeezed to dispense the saline solution L from the inverted container 112, the air pressure within the clearance space C between the bag 119 and the wall 114 is squeezed against the bag 119 which then collapses and displaces the liquid A through the adapter flange 118a and then through the adapter passageway bore 130. The liquid flowing from the bore 130 is constrained by the diaphragm 124 and exerts the necessary threshold hydraulic pressure against the annular diaphragm portion 124e which is resiliently deflected to further compress the tubular valve portion 124dd against the boss 120f. The additional compression of the valve portion 124dd thereby displaces and unseats the sealing ring 125 from wall 118e to enable the liquid flow therebetween into the adjacent portion of the annular clearance A which is enlarged by the diaphragm deflection as shown in the entirely corresponding partial structure illustrated in FIG. 2A of the first embodiment of the nozzle assembly. The cap wall 120 has a narrow vent groove 120i which is located on the dry or non-liquid side above the outer portion of the diaphragm bead 124a to enable air displacement with the deflection of the diaphragm 124.

The liquid flow through the clearance space A leads to discharge of the liquid through the tubular nozzle 124d as indicated by the arrow B. The sealing ring 125 performs as a one-way valve allowing only outflow of dispensed liquid when the flexible wall 114 and bag 119 are squeezed, so that once the additional compression of the valve portion 124dd is relaxed when the manual squeeze is released, the residual compression of the valve portion 124dd will cause the sealing ring 125 to reseat and firmly seal against the wall 118e to close the one-way valve and prevent any backflow of liquid or air. Such backflow might otherwise occur, for example, should the dispenser become exposed to non-sterile fluid such as by dropping into contaminated liquid. The valve portion column 124dd thus acts as an integral and elastomeric biasing spring on the sealing ring 125.

In order to maintain the pressure in the expanding volume of the clearance space C as the liquid in the bag 119 is progressively emptied with successive dispensings and increasing collapse of the bag 119, an air aspiration conduit is provided through the nozzle assembly 100 leading to the air clearance C. Accordingly, when the manual squeezing of the container wall 114 is released, air enters the nozzle assembly 100 through an entrance passageway 126 through the cap 120 which downwardly directs the air to a valve seat 126a opening from the lower surface of the cap 120. The diaphragm 124 has a lateral extension portion 124f which seats on the valve seat 126a to form a one-way valve which is normally closed, particularly when the container wall 114 is squeezed and the air pressure in the clearance C is communicated against the interior surface of the diaphragm extension portion 124f. However, during air aspiration, the diaphragm extension 124f unseats from the valve seat 126a to open the one-way flow of air around the diaphragm extension 124f so that the air flows through an axially aligned passageway 127 through the adapter 118 leading to a radially aligned passageway 128 in the adapter 118. The inner end of the radial passageway 128 opens into an axial bore 129 formed through the adapter 118 adjacent to the outer surface of the cylindrical flange 118a. In order to prevent the diaphragm extension 124f from excessively deflecting against and otherwise closing the adapter passageway 127, a pair of small beads 127a or similar small projection are provided preferably adjacent the peripheral opening of the passageway 127 in order to engage the diaphragm extension 124f when it is deflected during air aspiration and thus maintaining clearance for air entry into the passageway 127.

From the bore 129 the aspirating air flows downwardly and is annularly distributed in the clearance space between the flange 118a and the bottleneck 116 and then passes through slots 131 formed through the annular lug 118aa leading to the air clearance C as indicated by the air flow path arrows D. In the arrangement provided in the structure of the second embodiment of the nozzle assembly, the aspirating air never comes in contact with the sterile liquid L contained within the sealed bag 119, and therefore the entirely separate liquid dispensing flow path and air aspiration flow path enable elimination of any filtering of the aspirating air which need not be sterile.

THIRD EMBODIMENT

Referring to FIG. 10, a third embodiment of the nozzle assembly in accordance with the invention and designated generally by reference character 210 is shown mounted on a molded plastic bottle container 212 for sterile liquid L with a squeezable wall 214. The container 212 opens at the top from a neck portion 216. An adapter portion 218 of the nozzle assembly generally closes the mouth of the neck 216 and has a cylindrical wall 218a which projects downwardly into the opening of the neck 216 with a radially flared, annular lug projection 218aa which securely seals against the interior surface of the neck. The upper surface of the adapter 218 supports a partitioned, elastomeric diaphragm 224 which integrally includes both air filtering portion 224a and a valve element portion 224dd as more fully described hereinafter. The elastomeric diaphragm 224 also includes a thickened, annular peripheral bead 224b which is clamped between the upper surface of the adapter 218 and the lower surface of an overlying housing or cap member 220. The circumferential periphery of the upper wall of the adapter 218 is seated on an inner annular shelf 220a which projects radially inwardly from a downwardly extending cylindrical skirt portion 220b of the cap 220. The skirt 220b also has a radially inwardly projecting annular lug 220c which is forced between a pair of adjacent annular coupling flanges 216a and 216b which enable an interference fit of the lug 220c therebetween to secure the clamping of the diaphragm 224 and adapter 218 on the bottleneck 216.

Referring particularly to FIGS. 11 and 12, in the illustrated embodiment, the air filter portion 224a of the integrated, elastomeric diaphragm 224 can be insert molded in which an annulus of the filter material is inserted during molding of the diaphragm 224 from elastomeric material, for example, silicone rubber. The filter material is embedded and supported at its inner periphery by the diaphragm valve portion 224*dd* and at the outer periphery by the bead 224*b* so that the annular medial portion is exposed to form the air filter portion 224*a*; for added structural integrity, the filter material may be embedded within radial ribs 224*c* of the elastomeric material. The filter membrane material of the portion 224*a* is hydrophobic to prevent passage of the sterile liquid L (saline solution) and is also impermeable to bacteria but is permeable to air so that the aspirating air is filtered to prevent entrained bacteria from contaminating the sterile liquid during aspiration as more fully described hereinafter; Suitable air permeable hydrophobic filter material for the diaphragm air filter portion 224*a* can be fabricated, for example, from supported acrylic copolymer treated with a siloxane composition such as the filter membrane material commercially available from Gelman Sciences in a particularly suitable composition designated Versapor-450 having a pore size of approximately 0.45 micron which is impenetrable by bacteria.

The diaphragm 224 also includes a tubular nozzle portion 224*d* which integrally extends upwardly from a larger elastomeric, tubular column or valve portion 224*dd*. The interior surface of the columnar valve portion 224*dd* fits loosely around a nipple formation 218*j* which projects upwardly from the upper wall of the adapter 218 to provide a conical clearance space A therebetween as best shown in FIG. 13B. The clearance space A leads to the central bore of the tubular portion 224*d* which has a liquid discharge orifice at its upper end indicated by arrow B.

The tubular nozzle portion 224*d* is supported by an annular boss 220*f* whose lower surface seals against the annular upper surface 224*ddd* of the tubular valve portion 224*dd*. A snap-fitting cover 220*g* connected to cap 220 is provided to removably fit over the tubular nozzle 224*d* and boss 220*f*.

The tubular column or valve portion 224*dd* extends downwardly and terminates in a tapered sealing ring 225 which normally seals, under compression by the boss 220*f* against the upper wall surface of the adapter 218 adjacently surrounding the nipple 218*j* to prevent leakage of the stored liquid L even under hydrostatic pressure when the container 212 is inverted during handling, and to prevent any backflow of non-sterile air or liquid from the clearance space A into the bottle neck 216. The backflow of liquid is additionally prevented by the projection of the conically shaped nipple 218*j* into the tubular nozzle portion 224*d* in order to minimize the volume of liquid remaining in the tubular portion 224 when the dispensing flow is stopped. The small amount of liquid remaining in the tubular portion 224*d*, which can be exposed to contamination by air, will be flushed out before the next dispensing.

Referring to FIGS. 10 and 13B, when the flexible container wall 214 is squeezed to dispense the liquid L from the inverted container 212 and nozzle assembly 210, the liquid flows through the passageway bore 228 and exerts the necessary threshold hydraulic pressure against the liquid-impermeable filter portion 224*a* of the diaphragm 224 which is resiliently deflected to further compress the tubular valve portion 224*dd* against the boss 220*f*; the additional compression of the valve portion 224*dd* thereby displaces and unseats the annular sealing ring 225, on the surface of the adapter 218 to enable the liquid flow therebetween into the adjacent portion of the annular clearance space A (which is enlarged by the diaphragm deflection). The cap 220 has a narrow vent groove 220*i* as shown in FIG. 10 which is located on the dry or non-liquid side above the diaphragm 224 to enable air displacement with the deflection of the diaphragm 224.

The liquid flow through the clearance space A leads to discharge of the liquid through the tubular nozzle 224*d* as indicated by the arrow B. The elastomeric valve portion 224*dd* and sealing ring 225 perform as a one-way valve allowing only outflow of dispensed liquid when the flexible container wall 214 is squeezed. Once the additional compression of the valve portion 224*dd* is relaxed when the manual squeeze is released, the residual compression of the valve portion 224*dd* will cause the sealing ring 225 to reseat and firmly seal against the wall of the adapter 218 to close the one-way valve and prevent any backflow of liquid or air. Such backflow might otherwise occur, for example, should the dispenser become exposed to non-sterile fluids such as by dropping into contaminated liquid The valve portion column 224*dd* thus acts as an integral and elastomeric biasing spring on the sealing ring 225.

Referring to FIG. 13A, in order to asperate air for reinflation of the squeeze flexible container wall 214 and to replace the liquid dispensed, ambient air is drawn into an entrance passageway 230 and is downwardly directed and filtered through the filter portion 224*a* above the passageway bore 228 through which the air flows through the adaptor skirt 218 and container neck and container neck 216. The filter portion 224*a* of the diaphragm 224 thus serves dual function as both the aspiration air filter as well as the hydraulically deflectable portion of the diaphragm valving in the liquid dispensing conduit. Accordingly, the integration of the hydraulically deflectable air filter within the diaphragm structure enables particularly uncomplicated flow path of the air aspiration conduit and a simplified nozzle assembly without jeopardizing contamination of the sterile liquid during storage and successive dispensing.

While particular embodiments of the invention have been shown and described in detail, it will be obvious to those skilled in the art that changes and modifications of the present invention, in its various aspects, may be made without departing from the invention in its broader aspects, some of which changes and modifications being matters of routine engineering or design, and others being apparent only after study. As such, the scope of the invention should not be limited by the particular embodiments and specific construction described herein but should be defined by the appended claims and equivalents thereof. Accordingly, the aim in the appended claims is to cover all such changes and modifications as fall within the true spirit and scope of the invention.

The invention is claimed as follows:

1. An elastomeric diaphragm structure for controlling liquid flow from a storage container or the like, integrally comprising; a resiliently deflectable valve element for biased sealing against a valve seat to form a one-way valve therewith and allowing only one-way flow of liquid therebetween when said valve element is resiliently unseated from the valve seat to open said valve; and an air filter portion integrally formed with said valve element, for filtering air aspiration into said storage container.

2. The diaphragm structure according to claim 1, wherein said air filter portion is deflectable under liquid flow pressure during dispensing of liquid from said container.

3. The diaphragm structure according to claim 2, wherein said deflectable valve element and said air filter portion are arranged adjacently within said diaphragm structure such that said deflection of said air filter portion induces deflection and opening of said valve element to enable passage of said liquid therethrough during dispensing discharge from said container.

4. The diaphragm structure according to claim 1, wherein said air filter portion is integrated by insertion during molding of said diaphragm structure.

5. The diaphragm structure according to claim 1, wherein said air filter portion is impermeable to both bacteria and flow of said liquid therethrough and is permeable to air thereby enabling only aspiration of air through said filter portion.

6. The diaphragm structure according to claim 1, wherein said air filter portion comprises an annular configuration surrounding said valve element.

7. A liquid dispensing nozzle assembly for mounting on a liquid container and dispenser having a flexible wall and liquid storage cavity for manually squeezed dispensing of liquid from the cavity through the nozzle assembly and for maintaining the liquid, such as contact lens saline solution, in sterile condition during storage and repeated dispensing of the liquid from the container cavity, said nozzle assembly comprising: a liquid discharge port; liquid conduit means for communication from the container cavity to said liquid discharge port to enable dispensing of said liquid through said port during said manually squeezed liquid dispensing; an air aspiration conduit means for aspirating air into said cavity to replace the liquid dispensed therefrom; and a partitioned diaphragm means integrally including a deflectable valve element within said liquid conduit means and a filter portion within said air aspiration conduit.

8. The nozzle assembly according to claim 7, wherein said filter portion is impermeable to both bacteria and flow of said liquid therethrough and is permeable to air thereby enabling only aspiration of air through said filter portion.

9. The nozzle assembly according to claim 8, wherein said filter portion forms an enclosing wall within said liquid conduit means.

10. The nozzle assembly according to claim 9, wherein said filter portion is deflectable under liquid flow pressure during dispensing of liquid through said liquid conduit means.

11. The nozzle assembly according to claim 10, wherein said deflectable valve element and said filter portion are arranged adjacently within said diaphragm means such that said deflection of said filter portion induces deflection and opening of said valve element to enable passage of said liquid therethrough for dispensing discharge from said nozzle assembly.

12. The nozzle assembly according to claim 11, wherein said filter portion comprises an annular configuration surrounding said valve element.

13. The nozzle assembly according to claim 7, wherein said diaphragm means comprises an integrally molded elastomeric diaphragm in which said filter portion is integrated by insertion during molding of said diaphragm.

14. A valve structure for controlling liquid flow from a nozzle structure on a liquid storage container or the like, comprising a resiliently deflectable valve element for biased sealing against a valve seat to form a one-way valve therewith and allowing only one-way flow of liquid therebetween when said valve element is resiliently unseated from the valve seat to open said valve, said valve element comprising a compressible column having opposing axial end surfaces which are normally compressed against respective valve surfaces of said nozzle structure including said valve seat for preventing said liquid flow through said valve, said column being further compressible to resiliently unseat one of said column end surfaces from said valve seat to allow said one-way liquid flow while said opposing column end surface remains stationary and compressed against said respective valve surface.

15. A valve structure according to claim 14, further comprising an elastomeric diaphragm member peripherally secured to said column for exertion of said hydraulic pressure against said diaphragm member in order to produce resilient deflection of said diaphragm member and said further compression of said column and said resilient unseating thereof with said diaphragm deflection.

16. A valve structure according to claim 15, wherein said diaphragm member includes an annular configuration peripherally joined to a generally cylindrical side surface of said column between the end surfaces thereof.

17. A valve structure according to claim 16, wherein said column has a generally cylindrical configuration peripherally joined to a central tubular portion projecting therefrom for discharge of said liquid therethrough.

18. A valve structure according to claim 14, in combination with said nozzle structure for mounting on said liquid storage container having a flexible wall and liquid storage cavity enabling manually squeezed dispensing of liquid from the cavity through the nozzle structure and for maintaining the liquid, such as contact lens saline solution, in sterile condition during storage and repeated dispension of the liquid from the container cavity, and wherein said nozzle structure comprises a liquid discharge port; liquid conduit means for communication from the container cavity to said liquid discharge port to enable dispensing of said liquid through said port during said manually squeezed liquid dispensing; and an air aspiration conduit means separate from said liquid conduit means for aspirating air into said cavity to replace the liquid dispensed therefrom, wherein said one-way valve controls flow of liquid within said liquid conduit means.

19. The combination according to claim 3, further comprising diaphragm means having a first portion including said compressible column defining said valve element, and a second portion defining a portion of said air aspiration conduit means.

20. A combination according to claim 19, wherein said second portion comprises at least one aperture formed in said diaphragm means for air flow therethrough.

21. A combination according to claim 20, further comprising an air permeable and bacteria impermeable filter member covering said at least one aperture for preventing entrainment of bacteria with said aspirating air flow into said liquid container cavity.

22. A combination according to claim 21, wherein a plurality of said apertures are formed in said diaphragms and are covered by respective portions of said filter member, and wherein said air aspiration conduit means is configured so as to direct said aspirating air through at least two of said apertures and corresponding filter portions in a sequential manner whereby said aspirating is filtered at least twice prior to entering said liquid container cavity.

23. A combination according to claim 21, wherein said filter member and diaphragm are carried between an adapter element and nozzle housing comprised within said nozzle structure.

24. A combination according to claim 23, wherein said adapter element includes separate passageways for communication between said liquid container cavity and said respective liquid and air aspiration conduit means.

25. The combination according to claim 19, wherein said diaphragm means further comprises a tubular portion and wherein said open valve directs said liquid flow therefrom into said tubular portion.

26. A combination according to claim 25, wherein said liquid discharge port is defined at one end of said tubular portion.

27. The combination according to claim 19, wherein said diaphragm means comprises an integrally molded elastomeric diaphragm.

28. A combination according to claim 19, further including means for holding said second portion of said diaphragm means stationary during air flow through said air aspiration conduit.

29. A combination according to claim 18, further comprising an air permeable and bacteria impermeable filter member and wherein said air aspiration conduit means comprises at least two passageways covered by separate portions of said filter member and wherein the configuration of said air aspiration conduit means is such as to direct air flow through said two portions of said filter member in a sequential manner whereby said aspirating air is filtered at least twice prior to entering said liquid containing cavity to prevent entrainment of bacteria with the aspiration air flow into said liquid container cavity.

30. A combination according to claim 29, wherein said filter member is hydrophobic in order to prevent permeation of the filter member by the liquid and thereby facilitate aspirating air flow therethrough.

31. A valve structure according to claim 14, in combination with said nozzle structure for mounting on a liquid container and dispenser having a flexible wall and liquid storage cavity enclosed within an inner flexible envelope within said flexible wall for manually squeezed dispensing of liquid from the cavity through the nozzle structure and for maintaining the liquid, such as contact lens saline solution, in sterile condition during storage and repeated dispensing of the liquid from said inner envelope, wherein said nozzle structure comprises a liquid conduit including a liquid discharge port for communication from the storage cavity within said inner envelope to discharge said liquid through said discharge port during said manually squeezed liquid dispensing; and an air aspiration conduit separate from said liquid conduit for aspirating air within said flexible wall of said container; and wherein said one-way valve controls flow of said liquid within said liquid conduit.

32. A combination according to claim 31, further including diaphragm means comprising a first portion including said compressible column and a second portion defining a portion of said air aspiration conduit means.

33. A combination according to claim 32, wherein said diaphragm means comprises an integrally molded elastomeric diaphragm.

34. A combination according to claim 33, wherein said diaphragm means further comprises a tubular portion and wherein said valve element is deflectable to permit said liquid flow past said valve element into said tubular portion.

35. A combination according to claim 31, in further combination with said inner envelope and wherein said air aspiration conduit is in communication with an air chamber at least partially surrounding said inner envelope.

36. An elastomeric diaphragm structure for controlling liquid flow from a storage container or the like, comprising an integral resiliently deflectable valve element for biased sealing against a valve seat to form a one-way valve therewith and allowing only one-way flow of liquid therebetween when said valve element is resiliently unseated from the valve seat to open said valve, and a tubular portion integrally formed with said valve element such that said resilient unseating of said valve element to open said valve permits said liquid flow past said valve element into said tubular portion for discharge therefrom, said valve element comprising an elastomeric annular column including first and second generally axially opposing annular surfaces which are normally compressed against respective valve surfaces of a nozzle structure including said valve seat for preventing said liquid flow through said valve, said column being further compressible to resiliently unseat one of said opposing annular surfaces from said valve seat to allow said one-way liquid flow while said opposite annular surface remains stationary and compressed against said valve surface.

37. A diaphragm structure according to claim 36, wherein said elastomeric annular column forms an outwardly flared annular base portion at one end of said tubular portion.

38. An elastomeric diaphragm structure for controlling liquid flow from a storage container or the like, comprising an integral resiliently deflectable valve element for biased sealing against a valve seat to form a one-way valve therewith and allowing only one-way flow of liquid therebetween when said valve element is resiliently unseated from the valve seat to open said valve, and a tubular portion integrally formed with said valve element such that said resilient unseating of said valve element to open said valve permits said liquid flow past said valve element into said tubular portion for discharge therefrom, said valve element comprising a compressible spring means which is normally compressed against said valve seat for preventing said liquid flow through said valve, said spring means being further compressible by sufficient hydraulic pressure by said liquid to unseat said spring means from said valve seat for said one-way flow.

39. A valve structure for controlling liquid flow from a nozzle structure on a liquid storage container or the like, comprising a tubular element for discharge of said liquid therethrough and a resiliently deflectable valve element for biased sealing against a valve seat to form a one-way valve therewith, said valve element comprising a compressible column formed adjacent said tubular element and having a sealing ring at one end thereof normally compressed against said valve seat to prevent said liquid flow through said valve, said column being further compressible to resiliently unseat said sealing ring from said valve seat to allow said one-way liquid flow into said tubular element for discharge therefrom.

40. A valve structure according to claim 39, further comprising an elastomeric diaphragm member peripherally secured to said column for exertion of hydraulic pressure from said liquid against said diaphragm member in order to produce resilient deflection of said diaphragm member and said further compression of said column to unseat said sealing ring.

41. A valve structure according to claim 40, wherein said diaphragm member includes an annular configuration peripherally joined to a generally cylindrical side surface of said column.

42. A valve structure for controlling liquid flow from a nozzle structure on a liquid storage container or the like, comprising a resilient deflectable valve element for biased sealing against a valve seat to form a one-way valve therewith and allowing only one-way liquid flow therebetween when said valve element is resiliently unseated from said valve seat to open said valve, said valve element comprising a compressible column having an axial end surface normally compressed against said valve seat for preventing said liquid flow through said valve, said column being further compressible to resiliently unseat said column end surface from said valve seat to allow said one-way liquid flow; and an elastomeric diaphragm member peripherally secured to said column for exertion of hydraulic pressure from said liquid against said diaphragm member in order to produce resilient deflection of said diaphragm member and said further compression of said column and said unseating of said column end surface with said diaphragm deflection.

43. A valve structure according to claim 42, wherein said column has a generally cylindrical configuration peripherally joined to a central tubular portion projecting therefrom for discharge of said liquid therethrough.

44. A valve structure according to claim 43, wherein said column, diaphragm member and tubular portion are integrally molded.

45. A valve structure according to claim 42, wherein said diaphragm member includes an annular configuration peripherally joined to a generally cylindrical side surface of said column.

* * * * *

UNITED STATES PATENT AND TRADEMARK OFFICE
CERTIFICATE OF CORRECTION

PATENT NO. : 5,025,957

DATED : June 25, 1991

INVENTOR(S) : Joseph V. Ranalletta, Fred E. Williams, Jr. and Rowland W. Kanner It is certified that error appears in the above-identified patent and that said Letters Patent is hereby corrected as shown below:

Column 12, line 55 (claim 19)  "The combination according to claim 3,"

should read -- The combination according to claim 18, --

Signed and Sealed this

Sixth Day of July, 1993

Attest:

MICHAEL K. KIRK

Attesting Officer

Acting Commissioner of Patents and Trademarks